United States Patent
Li et al.

(10) Patent No.: US 10,004,917 B2
(45) Date of Patent: Jun. 26, 2018

(54) NEURAL PROSTHETIC DEVICE AND METHOD OF MAKING SAME

(71) Applicant: Board of Trustees of Michigan State University, East Lansing, MI (US)

(72) Inventors: Wen Li, East Lansing, MI (US); Ki Yong Kwon, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 37 days.

(21) Appl. No.: 14/317,301

(22) Filed: Jun. 27, 2014

(65) Prior Publication Data
US 2015/0018901 A1    Jan. 15, 2015

Related U.S. Application Data

(60) Provisional application No. 61/845,106, filed on Jul. 11, 2013.

(51) Int. Cl.
*A61N 5/06* (2006.01)

(52) U.S. Cl.
CPC ......... *A61N 5/0601* (2013.01); *A61N 5/0622* (2013.01); *A61N 2005/0652* (2013.01); *A61N 2005/0663* (2013.01); *Y10T 29/4913* (2015.01)

(58) Field of Classification Search
None
See application file for complete search history.

(56) References Cited

U.S. PATENT DOCUMENTS 6,389,313 B1 * 5/2002 Marchitto .............. A61B 18/22
                                                        604/21
6,458,157 B1 * 10/2002 Suaning ................. A61F 2/14
                                                        623/6.63

(Continued)

FOREIGN PATENT DOCUMENTS

WO    WO 2011057276 A2 *  5/2011   ......... A61B 5/04001
WO    WO 2012023086 A1 *  2/2012   ........... A61N 5/0613

OTHER PUBLICATIONS

Kwon et al., Opto-µECoG Array: Transparent µECoG Electrode Array and Integrated LEDs for Optogenetics, IEEE Biomedical Circuits and Systems Conference (BioCAS 2012), Nov. 2012.*

(Continued)

*Primary Examiner* — Lynsey Eiseman
*Assistant Examiner* — Manolis Pahakis
(74) *Attorney, Agent, or Firm* — Schwegman Lundberg & Woessner, P.A.

(57) ABSTRACT

A neural prosthetic device can selectively deliver light to different cortical layers, at different depths, in the brain. The device includes LEDs and corresponding waveguides that can extend into the brain. At least two of the waveguides have different lengths. The neural prosthetic device or other devices can be manufactured by changing the hydrophilicity or lyophilicity of a portion of a substrate layer, then depositing uncured polymer on the treated portion of the substrate layer. The uncured polymer flows under the influence of surface tension to form a volume. The volume is shaped as a dome that extends laterally to a boundary between the treated and untreated portions. The polymer is cured in discrete regions through the substrate layer. The discrete regions extend longitudinally from the substrate layer to a curved surface of the dome. The uncured portion of the (Continued)

polymer is removed. The cured regions form the waveguides.

11 Claims, 6 Drawing Sheets

(56) References Cited

U.S. PATENT DOCUMENTS

| | | | | |
|---|---|---|---|---|
| 7,027,874 | B1* | 4/2006 | Sawan | A61N 1/0551 607/116 |
| 7,288,108 | B2* | 10/2007 | DiMauro | A61N 5/0601 128/898 |
| 7,883,536 | B1* | 2/2011 | Bendett | A61N 5/0603 607/88 |
| 8,372,726 | B2* | 2/2013 | de Graff | H01L 27/14618 257/786 |
| 2002/0161417 | A1* | 10/2002 | Scribner | A61N 1/36046 607/54 |
| 2003/0039455 | A1* | 2/2003 | Ouchi | G02B 6/1221 385/88 |
| 2003/0083724 | A1* | 5/2003 | Jog | A61N 1/0536 607/122 |
| 2003/0089914 | A1* | 5/2003 | Chen | H01L 33/54 257/79 |
| 2003/0233138 | A1* | 12/2003 | Spooner | A61B 18/203 607/93 |
| 2004/0199235 | A1* | 10/2004 | Younis | A61N 1/0534 607/116 |
| 2004/0236231 | A1* | 11/2004 | Knighton | A61B 1/00165 600/476 |
| 2005/0237739 | A1* | 10/2005 | Lee | A61N 5/0613 362/241 |
| 2006/0217787 | A1* | 9/2006 | Olson | A61N 5/0616 607/88 |
| 2006/0247754 | A1* | 11/2006 | Greenberg | A61N 1/0543 607/137 |
| 2007/0197892 | A1* | 8/2007 | Shen | A61B 5/04001 600/378 |
| 2007/0233208 | A1* | 10/2007 | Kurtz | A61N 5/0613 607/88 |
| 2008/0033519 | A1* | 2/2008 | Burwell | A61N 5/0601 607/122 |
| 2008/0288036 | A1* | 11/2008 | Greenberg | A61N 1/0541 607/115 |
| 2008/0297910 | A1* | 12/2008 | Bhandari | B29D 11/00365 359/648 |
| 2008/0306576 | A1* | 12/2008 | Boyden | A61N 5/0618 607/91 |
| 2009/0118800 | A1* | 5/2009 | Deisseroth | A61N 5/0603 607/92 |
| 2009/0204185 | A1* | 8/2009 | De Kok | A61N 5/0613 607/88 |
| 2009/0264972 | A1* | 10/2009 | Zhou | A61N 1/0543 607/116 |
| 2010/0049178 | A1* | 2/2010 | Deem | A61B 18/02 606/9 |
| 2010/0249890 | A1* | 9/2010 | Choi | A61N 5/0613 607/92 |
| 2011/0087311 | A1* | 4/2011 | Zorzos | A61N 5/0601 607/89 |
| 2011/0106229 | A1* | 5/2011 | Ortmann | A61B 5/04001 607/116 |
| 2011/0112591 | A1* | 5/2011 | Seymour | A61B 5/0084 607/3 |
| 2011/0230747 | A1* | 9/2011 | Rogers | A61B 5/05 600/377 |
| 2012/0165759 | A1* | 6/2012 | Rogers | A61B 5/6867 604/264 |
| 2012/0295376 | A1* | 11/2012 | Lee | A61N 5/0622 438/28 |
| 2013/0131485 | A1* | 5/2013 | Oh | A61N 1/0529 600/393 |
| 2013/0237906 | A1* | 9/2013 | Park | A61N 1/0551 604/93.01 |
| 2014/0350375 | A1* | 11/2014 | Wolfe | A61B 5/0084 600/377 |

OTHER PUBLICATIONS

Zhang et al., Integrated device for optical stimulation and spatiotemporal electrical recording of neural activity in light-sensitized brain tissue, Neural Eng. Oct. 2009.*

Chen et al., A fiber-based implantable multi-optrode array with contiguous optical and electrical sites, J. Neural Eng. 10 (Jul. 24, 2013).*

Kim et al., Parylene-C-Coated Indium Tin Oxide Electrodes for the Optical- and Electrical-Impedance Characterization of Cells, J. Nanosci. Nanotechnol. Jul. 2012, vol. 12, No. 7.*

Zorzos et al., Three-dimensional multiwaveguide probe array for light delivery to distributed brain circuits, Optics Letters, Dec. 1, 2012, vol. 37, No. 23.*

Wang et al., Integrated device for combined optical neuromodulation and electrical recording for chronic in vivo applications, J. Neural Eng. 9 (Dec. 7, 2012).*

Abaya et al., Characterization of a 3D optrode array for infrared neural stimulation, vol. 3, No. 9, Biomedical Optics Express, Aug. 24, 2012.*

Ledochowitsch et al., A Transparent µECoG Array for Simultaneous Recording and Optogenetic Stimulation, Conf Proc IEEE Eng Med Biol Soc. 2011;2011:2937-40.*

Kwon et al., Integrated Slanted Microneedle-LED Array for Optogenetics, 35th Annual International Conference of the IEEE EMBS, Osaka, Japan, Jul. 3-7, 2013.*

Kwon et al., Integrated Multi-LED Array With Three-Dimensional Polymer Waveguide for Optogenetics, MEMS 2013, Taipei, Taiwan, Jan. 20-24, 2013.*

Bhandari et al., A Novel Method of Fabricating Convoluted Shaped Electrode Arrays for Neural and Retinal Prostheses, Sens Actuators A Phys. 2008 ; 145-146(1-2): 123-130.*

Koo et al., Arrowhead-Shaped Microelectrodes Fabricated on a Flexible Substrate for Enhancing the Spherical Conformity of Retinal Prostheses, Journal of Microelectromechanical Systems, vol. 20, No. 1, Feb. 2011.*

Huang, H, et al., "Different fabrication methods of out-of-plane polymer hollow needle arrays and their variations", Institute of MEMS, National Tsing-Hua University, No. 101, Kuang-Fu Rd., Sec. II, Hsinchu 300, Taiwan E-mail: ccfu@mx.nthu.edu.tw, (Jan. 25, 2007), 11 pgs.

Huang, H, et al., "Different fabrication methods of out-of-plane polymer hollow needle arrays and their variations", Institute of MEMS, National Tsing-Hua University, No. 101, Kuang-Fu Rd., Sec. II, Hsinchu 300, Taiwan E-mail: ccfu@mx.nthu.edu.tw Received Oct. 28, 2006, in final form Jan. 3, 2007 Published Jan. 25, 2007 Online at stacks.iop.org/JMM/17/393, (Jan. 25, 2007), 393-402.

Kwon, K., et al., "Integrated Multi-LED Array With Three-Dimensional Polymer Waveguide for Optogenetics", (2013), 4 pgs.

Kwon, Ki Yong, et al., "Droplet Backside Exposure for Making Slanted SU-8 Microneedles", Research supported by National Science Foundation and Michigan State University. K. Kwon, X. Bi, and W. Li are with the Electrical and Computer Engineering Department, Michigan State University, East Lansing, MI 48824 USA (phone: +1-517-353-7832, e-mail:, (2013), 4 pgs.

Kwon, Ki Yong, et al., "Integrated Slanted Microneedle-LED Array for Optogenetics", Research supported by National Science Foundation and Michigan State University. K. Kwon and W. Li are with the Electrical and Computer Engineering Department, Michigan State University, East Lansing, MI 48824 USA (phone: +1-517-353-7832, e-mail: kwonki3, (2013), 4 pgs.

Kwon, Ki Yong, et al., "Opto- ECoG Array: A Hybrid Neural Interface with Transparent ECoG Electrode Array and Integrated LEDs for Optogenetics", TBioCAS-2013-Mar-0040-BioCAS-2012.

(56) References Cited

OTHER PUBLICATIONS

R2—This work was supported in part by Michigan State University and the Electrical, Communications and Cyber Systems Division of the National Science Foundation under the Award No. ECCS-1055269. K. Kwon, B. Sirowatka (Mar. 1, 2013), 8 pgs.

Lee, Hyung-Min, et al., "A Power-Efficient Wireless Capacitor Charging System Through an Inductive Link", IEEE Transactions on Circuits and Systems—11: Express Briefs, vol. 60, No. 10, Oct. 2013, (Oct. 1, 2013), 707-711.

Lee, Hyung-Min, et al., "A Power-Efficient Wireless System With Adaptive Supply Control for Deep Brain Stimulation", IEEE Journal of Solid-State Circuits, vol. 48, No. 9, Sep. 2013, (Sep. 1, 2013), 14 pgs.

McAllister, Devin V., et al., "Microfabricated needles for transdermal delivery of macromolecules and nanoparticles: Fabrication methods and transport studies", www.pnas.org/cgi/doi/10.1073/pnas.2331316100 PNAS—Nov. 25, 2003 vol. 100 No. 24 13755-13760, (Nov. 25, 2003), 6 pgs.

Yizhar, Ofer, et al., "Optogenetics in Neural Systems", 1Department of Bioengineering 2Department of Psychiatry and Behavioral Sciences—Neuron 71, Jul. 14, 2011 "2011 Elsevier Inc, 3CNC Program, 4Howard Hughes Medical Institute Stanford University, Stanford, CA, 94305, USA *Correspondence: deissero@stanfor, (Jul. 14, 2011), 26 pgs.

Yizhar, Ofer, et al., "Optogenetics in Neural Systems", Neuron 71, Jul. 14, 2011 "2011 Elsevier Inc—1Department of Bioengineering 2Department of Psychiatry and Behavioral Sciences—3CNC Program, 4Howard Hughes Medical Institute, Stanford University, Stanford, CA, 94305, USA *Correspondence: deissero@stanford., (Jul. 14, 2011), 9-34.

* cited by examiner

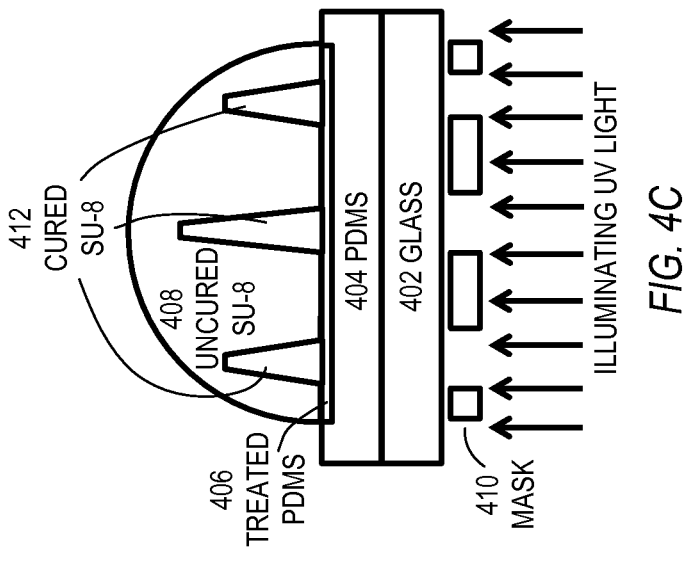
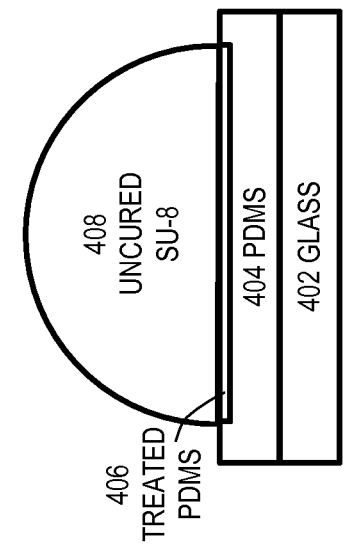
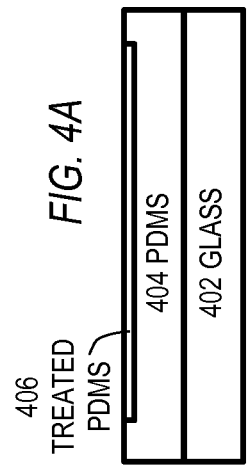
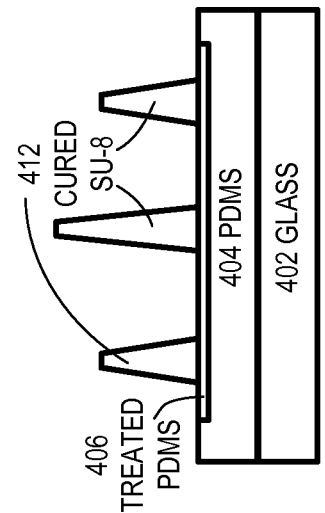

NEURAL PROSTHETIC DEVICE AND METHOD OF MAKING SAME

CLAIM OF PRIORITY

This application claims priority to U.S. Provisional Application No. 61/845,106, filed Jul. 11, 2013, which is incorporated by reference herein in its entirety.

BACKGROUND

A neuromodulation technique, known as optogenetics, involves directing light onto particular neurons in the brain. For instance, directing blue light onto particular neurons that are expressed channelrhodopsin-2 (ChR2) in the brain can stimulate neuronal activity. In some applications, the light can be used to control behavior in a subject. For experiments with freely behaving subjects, there are relatively few existing ways to deliver light to the subject. For instance, light may be delivered by an optical fiber, but the behavior of the subject may be influenced by the tether of the fiber. As another example, a head-mounted single light emitting diode (LED) system may be awkward, and may have relatively poor spatial resolution for light delivery inside the brain.

SUMMARY

A neural prosthetic device is discussed that can selectively deliver light to different depths. For instance, when used as a brain machine interface device, the neural prosthetic device can selectively deliver light to different cortical layers, at different depths, in the brain. The light is introduced into the brain tissue at the desired depth within the brain, rather than at a single depth that may be different than the desired depth. The device includes its own sources of light, rather than relying on a tethered optical fiber to deliver light to the device. This desirably frees a subject from the tether of an optical fiber, and allows the subject to move more freely and naturally. The neural prosthetic device can also be used to treat other neural diseases or injuries in a central nervous system or a peripheral nervous system, such as a spinal injury or Parkinson's disease.

The device includes a plurality of waveguides that can extend into the brain, where at least two of the waveguides have different lengths. The device includes a corresponding light emitting diode for each waveguide. By selectively activating an LED that corresponds with a waveguide of a particular length, a practitioner can precisely target one particular depth in the brain. The different waveguide lengths allow the practitioner to easily switch among the targeted depths, without removing or replacing any devices that interface with the brain. The LEDs can be powered controlled wirelessly.

In some examples, the device can also record electrical neural activity in the brain. The waveguides can include a metallic material on their exteriors. The metallic material can function as a recording electrode, which can record electrical activity at the depth of the waveguides. The metallic material can additionally preventing light leakage through side walls of the waveguides, and can thereby improve the light containment of the waveguides. The metallic material can be encased within a thin-film sandwich structure, which can reduce or eliminate light-induced electrical artifacts, such as those caused by the well-known Becquerel effect.

The device can be manufactured by changing the hydrophilicity (or lyophilicity) of a portion of a substrate layer, then depositing uncured polymer on the treated portion of the substrate layer. The uncured polymer flows under the influence of surface tension to form a volume. The volume is shaped as a dome that extends laterally to a boundary between the treated and untreated portions. The polymer is cured longitudinally in discrete regions through the substrate layer. The discrete regions extend longitudinally from the substrate layer to a curved surface of the dome. The uncured portion of the polymer is removed. The cured regions form the waveguides.

BRIEF DESCRIPTION OF THE FIGURES

FIGS. 4A-4E show an example of a manufacturing process for a neural prosthetic device, such as the device of FIG. 2.

DETAILED DESCRIPTION

Figure 1:
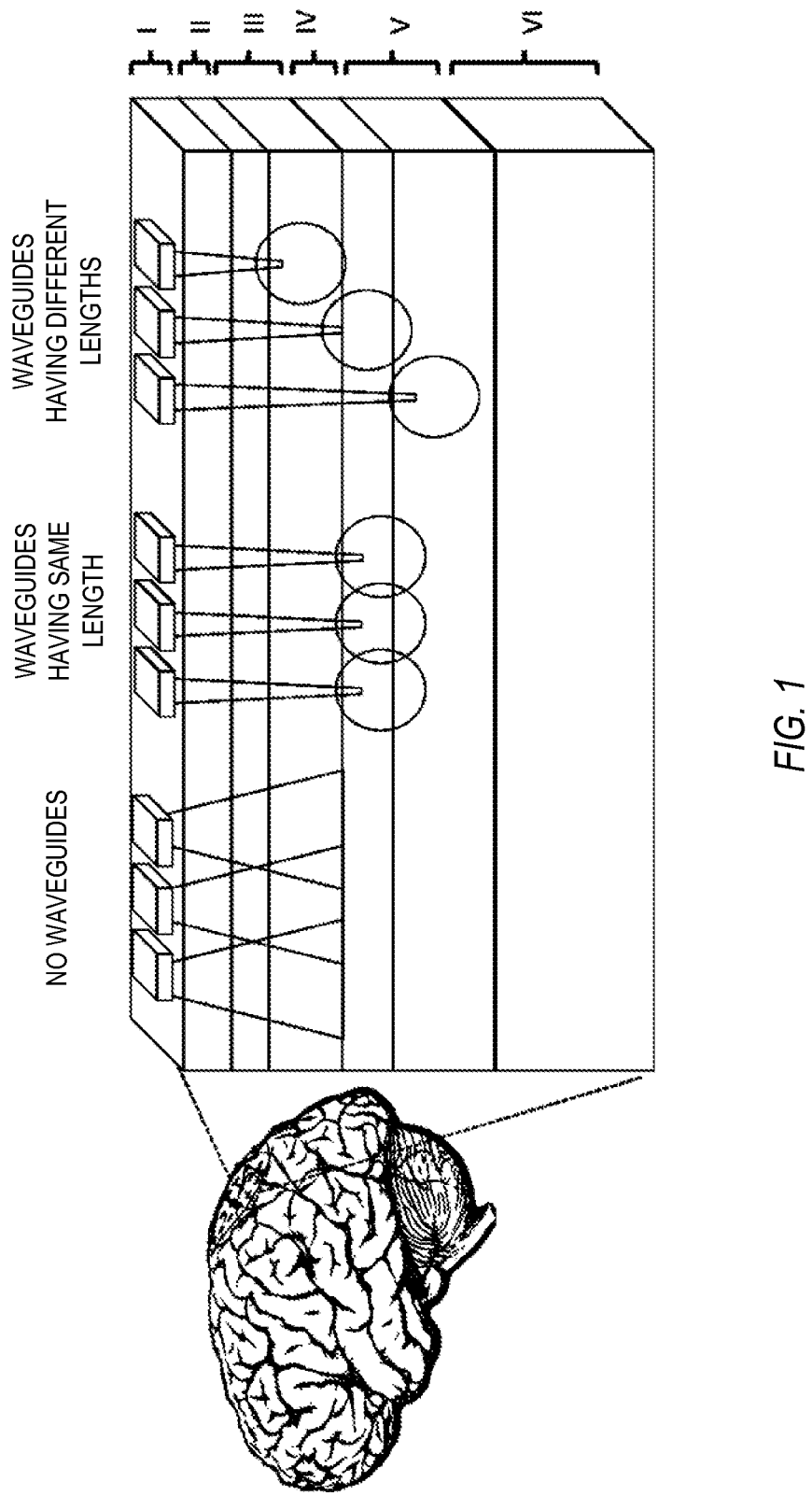
FIG. 1 is a comparison of tissue illumination without waveguides, tissue illumination using waveguides of a single length, and tissue illumination using waveguides having varying lengths.

FIG. 1 compares tissue illumination without waveguides, tissue illumination using waveguides of a single length, and tissue illumination using waveguides having varying lengths. Use of the array having different waveguide lengths allows a practitioner to controllably stimulate different cortical layers, which is difficult or impossible with surface stimulation or with an array of waveguides having the same length. In the example of FIG. 1, the cortical layers are labeled as I, II, III, IV, V, and VI. Use of surface stimulation (e.g., no waveguides) can lack the precision to stimulate only one or a small number of layers. Use of an array of waveguides having the same length can direct light with precision to a cortical layer, but lacks the flexibility to stimulate other cortical layers. In contrast, use of an array of waveguides having different lengths can selectively direct light to multiple layers. This is a significant advantage over use of no waveguides or use of an array of waveguides having the same length.

Figure 2:
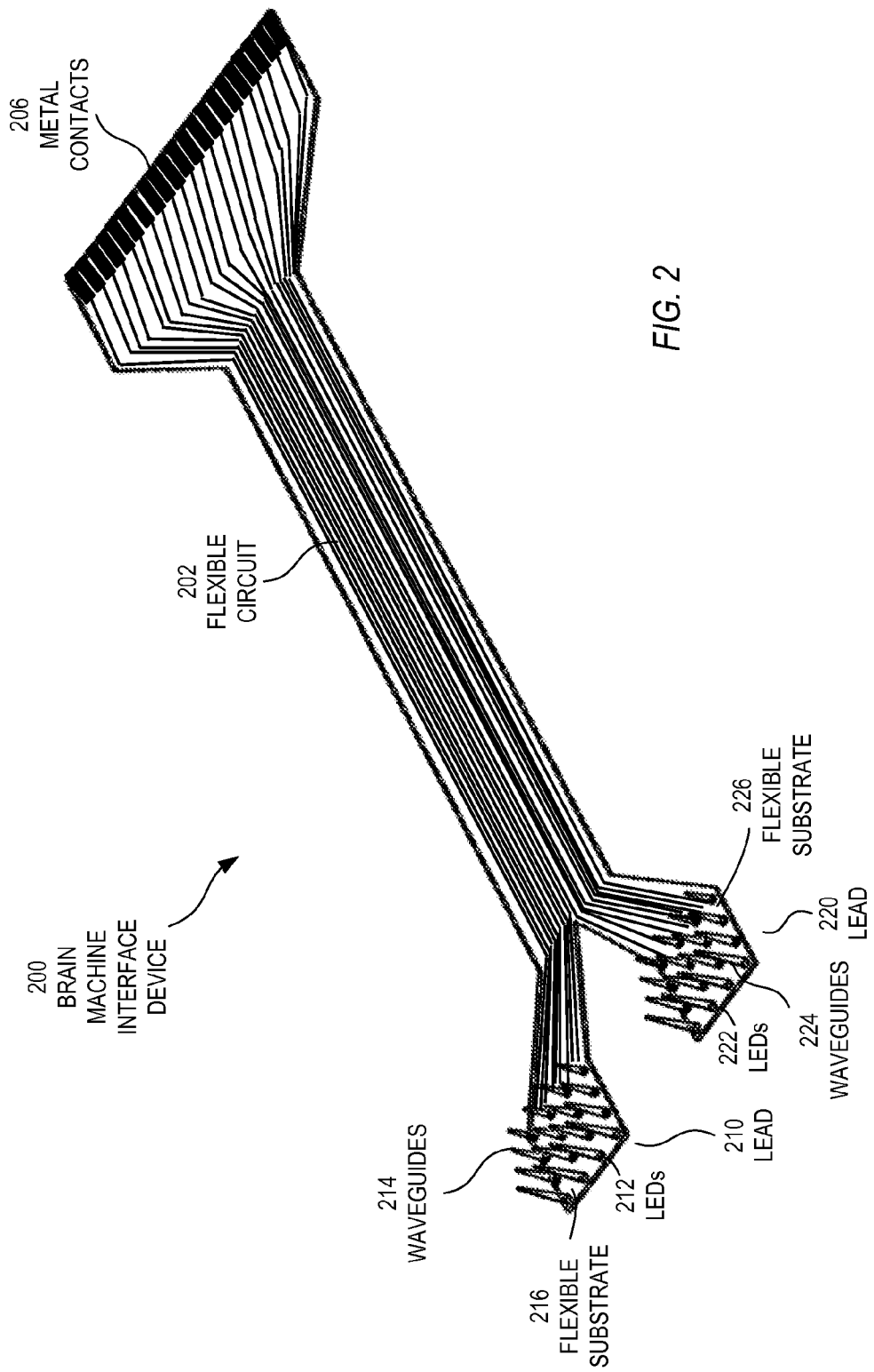
FIG. 2 is a plan drawing of an example of a neural prosthetic device.

FIG. 2 is a plan drawing of an example of a neural prosthetic device 200. In this example, the device is formed as a flexible circuit 202, with leads 210 and 220 and electrically conductive metal contacts 206 at opposite ends of the flexible circuit 202. The configuration of a flexible circuit 202 is but one example, and other suitable configurations may also be used. The use of two leads 210, 220 for a single set of contacts 206 is also an example; a flexible circuit may alternatively use one lead, three leads, four leads, or more than four leads. The two leads 210, 220 each include LEDs 212, 222, a flexible substrate 216, 226, and waveguides 214, 224.

Figure 3:
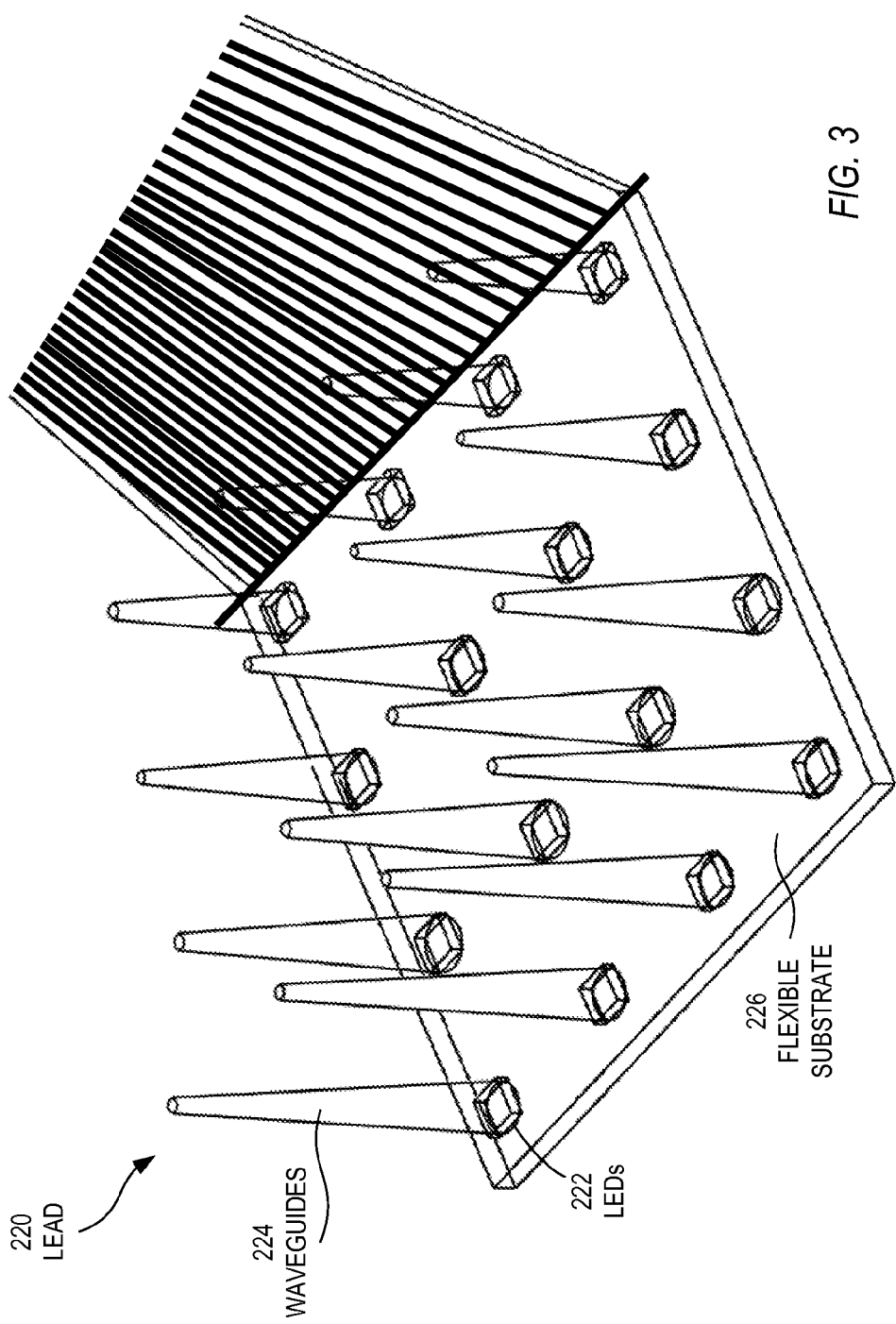
FIG. 3 is a schematic drawing of the LEDs, the flexible substrate, and the waveguides from the device of FIG. 2.

FIG. 3 more clearly shows one lead 220 from the neural prosthetic device 200 of FIG. 2. The other 210 of the two leads is similar in structure and function to lead 220.

The neural prosthetic device 200 includes a plurality of LEDs 222 spaced apart in a planar configuration. The planar configuration defines a lateral plane and defines a longitudinal direction perpendicular to the lateral plane. In some examples, the LEDs 222 are independently controllable. In some examples, the LEDs 222 emit light at the same wavelength. In some examples, the LEDs 222 emit light in the blue portion of the spectrum (e.g., with a wavelength between 450 nm and 495 nm). In other examples, the LEDs can emit in other portions of the spectrum, such as in the green, yellow, or red portions. In some examples, the LEDs 222 can emit different wavelengths, which can active different optogeneticopsins, such as mutations of ChR2, halorhodospin, and its mutations.

The neural prosthetic device 200 includes a transparent flexible substrate 226 is disposed parallel to the lateral plane and longitudinally adjacent to the plurality of LEDs 222. In some examples, the flexible substrate 226 is formed from a silicon-based organic polymer that is transparent over the range of emission wavelengths of the LEDs. In some examples, the flexible substrate 226 is formed from polydimethylsiloxane (PDMS).

The neural prosthetic device 200 also includes a plurality of transparent waveguides 224 in a one-to-one correspondence with the plurality of LEDs 222. Each waveguide 224 can have a first end proximate the flexible substrate 226 and a second end extending longitudinally away from the flexible substrate 226. The waveguides 224 and the LEDs 222 can be on opposite sides of the flexible substrate 226. Each waveguide 224 can receive light from a respective LED 222 through its first end, transmit the light longitudinally from its first end to its second end, and expel the light at its second end. Each waveguide 224 can have a length between its first and second ends. At least two of the waveguides 224 can have different lengths. When the neural prosthetic device 200 is placed onto a brain of a subject, the waveguides 224 can extend into the brain tissue to different depths, depending on the different lengths of the waveguides 224. By selectively switching among the LEDs, a practitioner can deliver light, through the corresponding waveguide 224, to the desired depth within the brain.

In some examples, at least one waveguide 224 is tapered to have a smaller cross-sectional area at its second end than at its first end. In some examples, the cross-sectional area of the first end of the waveguide 224 is smaller than a cross-sectional area of a corresponding LED 222. The tapering is believed to be caused by scattering and diffraction of ultraviolet light during a backside exposure process. As more light scatters, there is less light available for curing at the second end of the waveguides, and the taper angle of the waveguides increases. The scattering and diffraction appears to originate from propagation inside a glass substrate, from a mask to a photoresist layer. For a zero-thickness substrate, there would be a minimal amount of scattering and diffraction, and the taper angle of the waveguide would be zero or relatively small. As a thickness of the substrate increases, the distance between the mask and the photoresist layer increases, the scattering and diffraction increases, and the taper angle of the waveguide increases.

In some examples, the second ends of the waveguides 224 are configured to lie on a mathematically constructed surface, the mathematically constructed surface including a portion of a sphere. In some examples, the waveguides 224 are mechanically durable enough to penetrate brain tissue without breaking. In some examples, the waveguides 224 are formed from a polymer that is transparent over the range of emission wavelengths of the LEDs 222. In some examples, the waveguides 224 are formed from SU-8.

In some examples, the neural prosthetic device 200 is formed as a flexible circuit 202, with the LEDs 212, 222, flexible substrates 216, 226, and waveguides 214, 224 at a first end of the flexible circuit, and the LEDs 212, 222 being electrically connected to metal contacts 206 at a second end of the flexible circuit 202 opposite the first end.

In some examples, the neural prosthetic device 200 includes one or more batteries for powering the LEDs 212, 222. In some examples, the batteries are configured to be recharged inductively. In some examples, the neural prosthetic device 200 is configured to receive wireless signals that can control the LEDs 212, 222. For devices that include inductive recharging and wireless controlling, the devices can be free from wired connection, which is desirable.

Figure 5:
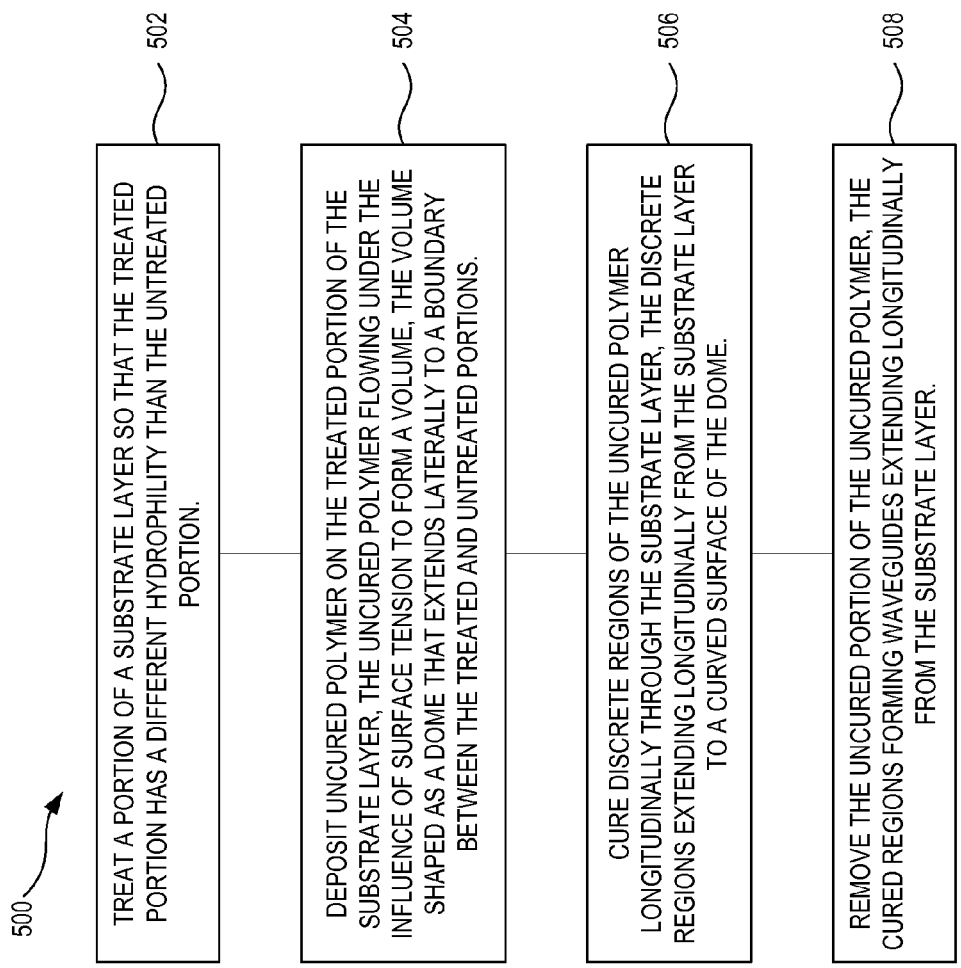
FIG. 5 is a flow chart of an example of a manufacturing process for an example of a neural prosthetic device, such as the device of FIG. 2.

FIGS. 4A-4E schematically show an example of a manufacturing process for a neural prosthetic device, such as the device 200 of FIG. 2. The manufacturing process is also shown in the flow chart of FIG. 5, which shows an example method 500 for manufacturing a neural prosthetic device, such as the device 200 of FIG. 2.

Step 502 treats a portion of a substrate layer so that the treated portion has a different hydrophilicity (or lyophilicity) than the untreated portion. For instance, by treating the substrate layer with oxygen plasma, the treated region can become more hydrophilic (or lyophilic) than the untreated region, so that the untreated region is more hydrophobic (or lyophobic) than the treated region. FIG. 4A shows the substrate layer as being formed from PDMS 404, with treated portion 406. The PDMS can be deposited on a glass substrate 402.

Step 504 deposits uncured polymer on the treated portion of the substrate layer. The uncured polymer flows under the influence of surface tension to form a volume. The volume is shaped as a dome that extends laterally to a boundary between the treated and untreated portions. FIG. 4B shows the uncured polymer SU-8 408 in a dome shape, after having flowed to the lateral edge of the treated portion 406.

Step 506 cures discrete regions of the uncured polymer longitudinally through the substrate layer. The discrete regions extend longitudinally from the substrate layer to a curved surface of the dome. FIG. 4C shows a mask 410 being used to allow discrete regions of illuminating ultraviolet light to pass through the glass 402 and the PDMS 404 to cure discrete volumes 412 in the SU-8 polymer. Note that the discrete volumes have different lengths, with the length varying over the lateral extent of the dome.

Step 508 removes the uncured portion of the uncured polymer. The cured regions form waveguides extending longitudinally from the substrate layer. FIG. 4D shows the uncured SU-8 408 having been removed, leaving the cured SU-8 412 regions that will form the waveguides.

FIG. 4E shows the substrate layer, PDMS 404, and the waveguides, cured SU-8 regions 412, removed from the glass substrate. In subsequent steps, the substrate layer and waveguides can be joined with the LEDs.

In some examples, the treated portion of the substrate layer is circular, and the dome has a circular boundary. In other examples, the treated portion may be square, rectangular, or have some other suitable shape. For those examples, the dome is bounded by the shape of the treated portion. In some examples, the substrate layer is formed from polydimethylsiloxane (PDMS). In some examples, the waveguides are formed from SU-8. In some examples, at least two of the waveguides have different longitudinal lengths. In some examples, the substrate layer, and attached waveguides, is affixed to a plurality of LEDs, each LED in the plurality being disposed adjacent to a respective waveguide. In some examples, the substrate layer and the waveguides are transparent at a wavelength emitted by the LEDs.

In some examples, the brain machine interface device, such as 200 (FIG. 2) can also record electrical neural activity in the brain. The waveguides can include a metallic material on their exteriors. The metallic material can function as a recording electrode, which can record electrical activity at the depth of the waveguides. The flexible circuit 202 (FIG. 2) can direct the recorded electrical activity through metal contacts 206 (FIG. 2) to a suitable processor.

The metallic material can additionally prevent light leakage through side walls of the waveguides, and can thereby improve the light containment of the waveguides. The metallic material can be encased within a thin-film sandwich structure, which can reduce or eliminate light-induced electrical artifacts.

Figure 6:
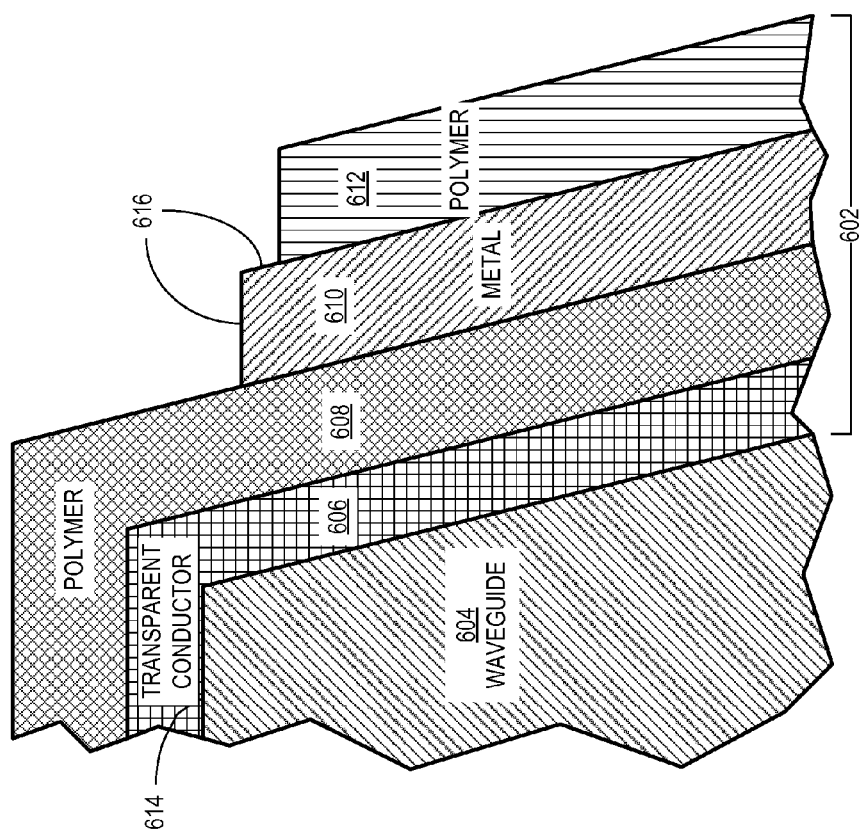
FIG. 6 is a close-up cross-sectional view of a tip of an example of a waveguide.

FIG. 6 is a close-up cross-sectional view of a tip of an example of a waveguide, such as 224 (FIG. 2). FIG. 6 shows a metallic material, included within a thin-film sandwich structure 602, deposited on the tip 614 of a waveguide 604. It will be understood that the number of layers, the materials and the thicknesses selected for the example of FIG. 6 are but one example; other configurations, materials and thicknesses can also be used.

The thin-film sandwich structure 602 includes a first layer 606 deposited on the waveguide 604. The first layer 606 is a transparent conductor, formed from a transparent conducting material, such as indium tin oxide (ITO). The first layer 606 functions as a shield, which can help reduce or prevent light-induced electrical artifacts, such as those caused by the well-known Becquerel effect. The first layer 606 can be relatively thin, with thicknesses that can be as low as a fraction of a micron or lower. As a result, the first layer 606 can extend over the tip of the waveguide 604.

The thin-film sandwich structure 602 includes a second layer 608 deposited on the first layer 606. The second layer 608 is a polymer layer, such as a chemical vapor deposited poly(p-xylylene) polymer, commonly known as Parylene. The second layer 608 functions as insulation between the first layer 606 and a third layer 610. Additionally, the second layer 608 helps encapsulate the waveguide 604 and other layers, which can improve biocompatibility. Polymers, such as Parylene, can be transparent or nearly transparent in the wavelengths of interest. As a result, the second layer 608 can extend over the first layer 606, over the tip 614 of the waveguide 604.

The thin-film sandwich structure 602 includes the third layer 610 deposited on the second layer 608. The third layer 610 is a metallic layer, such as gold. The third layer 610 is a good electrical conductor, and can deliver electrical signals from within the brain, proximate the tip of the waveguide 604, along the exterior of the waveguide 604, to the respective conductor on the flexible circuit 202 (FIG. 2). Additionally, the metallic layer can be relatively opaque at the wavelengths of interest, which can help contain light within the waveguide 604. As a result, the third layer 610 does not extend over the tip 614 of the waveguide 604, because to do so would obscure the light from the waveguide 604.

The thin-film sandwich structure 602 includes a fourth layer 612 deposited on the third layer 610. The fourth layer 612 is another polymer layer, such as Parylene. The fourth layer 612 encapsulates and electrically insulates the third layer 610. The fourth layer 612 leaves exposed a portion 616 of the third layer 610, so that the third layer 610 can electrically contact a relatively small portion of the brain during use. One advantage to exposing only a small portion 616 of the metallic layer, rather than the full metallic layer, is that the recorded electrical signals arise from a single depth within the brain, rather than from a range of depths between the waveguide tip and the surface of the brain. In the example of FIG. 6, the exposed portion 616 of the metallic layer is proximate the tip 614 of the waveguide 604. An advantage to having the exposed portions near the tips of the waveguides is that a user can correlate the received electrical signals with depth within the brain. In other examples, the fourth layer 612 can be configured to expose one or more other portions of the metallic layer, along the length of the waveguide 604.

The following sections describe an example neural prosthetic device that was manufactured and analyzed in a laboratory setting. The section "EXAMPLE DEVICE" discusses the configuration of the manufactured device. The section "MANUFACTURING PROCESS" discusses an example manufacturing process that was used to manufacture the device. The section "PROPERTIES" discusses the calculated optical properties and measured optical, electrical, and mechanical properties of the manufactured device. The section "DROPLET GEOMETRY" discusses the calculated and measured properties of a droplet that is used to form the curved interface, which is used in the example manufacturing process that was used to manufacture the device.

Example Device

An example neural prosthetic device was fabricated. The example device included 32 embedded LED light sources on a polyimide substrate. Polymer waveguides for the example device were fabricated separately on a PDMS substrate using a backside exposure technique and bonded with the multi-LED array using a shape-matching assembly. The example device measured 1.5 mm by 1.5 mm square, with 16 (4-by-4 grid) channels per each hemisphere to meet the specifications of bilateral visual cortices in rats. Integrated light sources allow the example device to be untethered, which is desirable for chronic implant in freely behaving animals. In addition, the use of an array having waveguides of different lengths improves the spatial resolution of the 3-D multi-LED array in depth.

Several design objectives were considered to design the optical stimulation array. As a first design objective, the waveguide should be able to deliver sufficient light to the desired cortical layer for evoking neural activity of the target neurons. A typical power density for activating ChR2 expressing neurons is about 1 milliwatt per square mm. The light sources used in the example device were LEDs, with a surface area of 220 μm by 270 μm. The waveguides in the example device had a base diameter of 200 μm. The LEDs were butt coupled into against the waveguides, so that light emitted from the LEDs was coupled efficiently into the respective waveguide. As a second design objective, the waveguide should be mechanically durable to penetrate the brain tissue without breaking, while minimizing damage to the brain tissue. In the example device, the waveguides were shaped as waveguides, with a relatively sharp tip and a relatively large supporting base. As a third design objective, the LEDs should be individually addressable and distributed over the targeting cortical area. In the example device, the LEDs were commercially-available parts sold by Cree, Inc, with a part number TR2227™. The TR2227™ LEDs were surface-mounted, with volumes of 220 μm by 270 μm by 50 μm, and a peak emission wavelength of 460 nm.

Manufacturing Process

The waveguide array can be fabricated separately on a PDMS substrate and bonded with the multi-LED array using shape-matching assembly. Within many available fabrication methods for waveguide structure, we chose a polymer (SU-8)-based backside exposure lithography technique. The use of lithography allows large scale, high-density systems to be fabricated at the wafer level.

For waveguide array fabrication, we used a new technique, known as droplet backside exposure (DBE), which utilizes the variation in the height profile of a droplet to create the array having waveguides of different lengths. The DBE method uses surface energy differences between two adjacent contact areas of a PDMS substrate to define the curvature of a droplet. A dome-shaped SU-8 droplet with a designed base size can be formed on a patterned hydrophilic (or lyophilic) area (02 plasma treated-PDMS surface) with hydrophobic (or lyophobic) surroundings (intact PDMS surface). In a certain volume range, the droplet is confined within the boundary between the hydrophilic (or lyophilic) and hydrophobic (or lyophobic) regions, due to the difference of the surface energies. Various heights of the droplet can then be achieved by controlling the volume of SU-8. Once the desired shape of the SU-8 droplet is formed, the waveguide structures can be constructed in the dome structure using the backside exposure. This technique allows us to control lengths, tip and bottom diameters of individual waveguides without sophisticated equipment and complex microfabrication techniques.

In order to reduce fabrication complexity, the multi-LED array and the waveguide array were fabricated and calibrated separately. Following calibration, the individual components were polymer bonded with SU-8. Detailed fabrication was divided into three steps: (1) Multi-LED array assembly, (2) waveguide fabrication and assembly, and (3) waveguide array fabrication and assembly.

The following is an example of a method for assembling the multi-LED assembly or array; other methods can also be used. Clean a 3-inch diameter silicon wafer. Spin-coat a 30 µm-thick layer of SU-8 polymer onto the wafer. Pattern the SU-8 layer as a mold for forming a PDMS stamp. Pour PDMS over the SU-8 mold to form the PDMS stamp. The stamp includes cavities that match the pattern of the LEDs. Cure the PDMS stamp for 40 minutes at 95 degrees C. Peel the PDMS stamp from the SU-8 mold. The PDMS stamp is retained for subsequent steps; the SU-8 mold can be discarded. Align 32 LED dies in the cavities of the PDMS stamp, with metal pads facing outward. Fabricate a 3-inch diameter wafer for the LED assembly. An example of a suitable material for the LED assembly substrate is Pyralux AP (AP7163E), which is commercially available from Dupont. Cut and clean the 3-inch diameter LED assembly substrate. Wet-etch the 3-inch diameter LED assembly substrate in copper. Apply a low-melting point solder on the contacts. An example of a suitable solder includes 144 ALLOY Field's Metal, which is commercially available from Rotometals, Inc., and has a melting point at 62 degrees C. Align the metal contacts of the LEDs on the PDMS stamp to the pre-soldered receiver sites on the LED assembly substrate. Heat the LED assembly substrate on a hot plate at 90 degrees C. for 30 seconds. Cool the LED assembly substrate to 40 degrees C. in air. Peel off the PDMS stamp from the LED assembly substrate. The LED assembly substrate is retained for subsequent steps; the PDMS stamp can be discarded. Submerge the LED assembly substrate, with the attached LEDs, in a hot acidic water bath, at 90 degrees C. and a pH of 2.0, for one minute. The preceding method can form the LED assembly substrate, on which the LEDs can be finely aligned, and on which the electrical connections can be formed in a self-aligning manner. Deposit a 5-micron-thick layer of Parylene-C by chemical vapor deposition (CVD) to protect the assembled LEDs.

The following is an example of a method for fabricating and assembling the waveguides; other methods can also be used. Clean a 3-inch diameter glass wafer. Bake and dehydrate the glass wafer. Spin-coat a 50 µm-thick layer of SU-8 polymer onto the glass wafer. Pattern the SU-8 layer as mock LEDs. Spin-coat a thin layer of PDMS onto the SU-8 layer to form cavities that match the shape of the LEDs. Cure the glass wafer at 95 degrees C. for 40 minutes. Treat the surface of the PDMS substrate with $O_2$ plasma. The $O_2$ treatment enhances adhesion between the SU-8 layer and the PDMS layer. Spin-coat an 800-µm-thick layer of SU-8 onto the $O_2$-treated PDMS layer. Pattern the backside exposure to form the waveguides. Develop the SU-8 layer. Polish the waveguide array with $O_2$ plasma. Release the PDMS layer from the glass wafer. Bond PDMS cavities onto their corresponding LEDs.

The following is an example of a method for fabricating and assembling the array of waveguides, without an oxide/polymer/metal/polymer sandwich structure on an exterior of the waveguides. Clean a 3-inch diameter glass wafer. Bake and dehydrate the glass wafer. Spin-coat a 50 µm-thick layer of SU-8 polymer onto the glass wafer. Pattern the SU-8 layer as mock LEDs. Spin-coat a thin layer of PDMS onto the SU-8 layer as mock LEDs. Cure the glass wafer at 95 degrees C. for 40 minutes. Deposit photoresist on the PDMS. Expose the photoresist in 7 mm-diameter circles. Treat the photoresist with $O_2$ plasma. The $O_2$ treatment converts the exposed hydrophobic (or lyophobic) areas to hydrophilic (or lyophilic) areas. Remove the photoresist. Deposit a 45 microliter volume of SU-8 on top of the $O_2$-treated PDMS, using a micropipette. Pattern the backside exposure to form the waveguides. Develop the SU-8. Polish the waveguide array with $O_2$ plasma. Release the layers from the glass wafer. The glass wafer may be discarded. Align the waveguide array onto corresponding LED chips. Bond the waveguide array to the corresponding LED chips with a polymer adhesive.

The following is an example of a method for fabricating and assembling the array of waveguides, including an oxide/polymer/metal/polymer sandwich structure on an exterior of the waveguides. Clean a 3-inch diameter glass wafer. Bake and dehydrate the glass wafer. Spin-coat a 50 µm-thick layer of SU-8 polymer onto the glass wafer. Pattern the SU-8 layer as mock LEDs. Spin-coat a thin layer of PDMS onto the SU-8 layer as mock LEDs. Cure the glass wafer at 95 degrees C. for 40 minutes. Deposit photoresist on the PDMS. Expose the photoresist in 7 mm-diameter circles. Treat the photoresist with $O_2$ plasma. The $O_2$ treatment converts the exposed hydrophobic (or lyophobic) areas to hydrophilic (or lyophilic) areas. Remove the photoresist. Deposit a 45 microliter volume of SU-8 on top of the $O_2$-treated PDMS, using a micropipette. Pattern the backside exposure to form the waveguides. Develop the SU-8. Polish the waveguide array with $O_2$ plasma. Deposit a 0.1-micron-thick layer of indium tin oxide (ITO) by DC sputtering. Deposit a 5-micron-thick layer of Parylene-C by chemical vapor deposition (CVD). Deposit a 1-micron-thick layer of gold (Au) by thermal evaporation. Wet etch the tip of the waveguide to remove any opaque material. Deposit a 5-micron-thick layer of Parylene-C, which can protect the previously-deposited layers. Remove the Parylene-C from the tip of the waveguide by reactive-ion etching (RIE) to expose the recording site. Release the layers from the glass wafer. The glass wafer may be discarded. Align the waveguide array onto corresponding LED chips. Bond the waveguide array to the corresponding LED chips with a polymer adhesive.

The structures used as waveguides for the neural prosthetic device could be configured as light guides for other purposes. The structure can include hollow channels formed by a multi-mask backside exposure lithography process. The multi-layer masking structure is constructed by patterning a first metal masking layer on the top side of a glass wafer, and then placing a second mask on the bottom side of the same wafer. After the backside exposure process, due to the different separations between the two masks and the bottom of the SU-8 droplet, the exterior wall of the tapered waveguide can have a larger inclining angle, while the interior wall has a smaller angle, resulting in a hollow needle structure. The hollow needle structure can be used for microfluidic channels in alternative devices. This method of manufacture can be utilized in manufacture of other devices that call for similar geometric structures. Such other devices could include, but not limited to, light waveguides, microfluidics, or communication pathways using optics or other methods.

Properties

The device described above, and manufactured in a laboratory setting using the manufacturing process described above, was measured to determine its optical properties, its electrical properties, and its mechanical properties. Each of these sets of properties is discussed in detail below.

Regarding the optical properties, we characterized the effect of the waveguide geometry on the irradiance and total flux of transmitted blue light, using a ray tracing method (TracePro®, Lambda Research Co., MA, USA). In the simulation, the average irradiance and the total flux were measured at a 100 μm distance from the waveguide tip, as functions of the tip size. With a small tip size, optical throughputs tended to spread out, resulting in divergent irradiance, while a large tip size resulted in concentrated irradiance with a confined output beam. The coupling efficiency of the proposed waveguide array was also studied. In this case, we assumed a typical LED radiation angle of about 60° and inserted an 80 μm-thick PDMS layer (with a refractive index of 1.46 at a wavelength of 470 nm) between the LED and the SU-8 waveguide (with a refractive index of 1.59 at a wavelength 470 nm). The estimated coupling efficiency of the waveguide was about 9%, which is close to the typical coupling efficiency of the butt coupling configuration. Based on the simulation results, one can select the tip size of the waveguide, which is important in order to deliver sufficient optical throughput to the target area, while permitting easy penetration of the tissue.

To characterize light scattering property of the array, we studied the optical throughput at the tip of the waveguide in a scattering media (20% w/w of gelatin). The 3-D multi-LED array was placed on the gelatin media and images of the optical throughput at the tip of the waveguide were captured. The activated LEDs were driven by 2.7 V, resulting in a power consumption of 3.4 mW, a temperature increase of 0.1° C., and the light source irradiance of 1 mW/mm². Blue light spectra (wavelength range of 450-495 nm) were extracted from the captured image, and the normalized relative light intensity (the maximum intensity as 1) showed a clear ellipsoidal scattering boundary (about 600 μm in length and about 100 μm in width) of the optical throughput. The clear ellipsoidal scattering boundary is desirable. Ultimately, the device can deliver a minimal irradiance of 1 mW/mm² to the target area to induce action potentials.

Regarding the electrical properties, for surface stimulation, an input voltage of about 2.7 V was used to drive a single LED chip to achieve the required optical power output, resulting in a power consumption of 3.4 mW. Considering 9% of the estimated coupling efficiency of the array, the LED chip was driven by an input voltage of 2.9 V to achieve an optical power intensity of 10 mW/mm². This resulted in a total power consumption of 17 mW and a temperature increase of about 0.4 degrees C. Further improvement can be envisioned by narrowing the radiation angle of the LED and optimizing the design of the waveguide.

Regarding the mechanical properties, mechanical reliability of the waveguide array was examined by a penetrating test. The waveguide array was inserted into and retracted from the 20% gelatin media 10 times, and cracks or breakages on the waveguide were examined under the microscope. With 10 samples, no visible damages were observed, indicating mechanical rigidity of the waveguide. The result suggested possible array implantation with intact dura, which helps minimize additional complications caused by a dura removal procedure. We also examined the flexibility of the array by implanting the array on curved gelatin surfaces with different curvatures. The flexible PDMS substrate wrapped around the curved surfaces, while the waveguide structures penetrated perpendicular to the surface. A combination of the flexible substrate and the rigid waveguide structure made possible a potential application for not only cortical implant but also spinal cord and peripheral nerves implants. Specifically for peripheral nerve implant, with the array having waveguides of different lengths, each row of waveguides can access different depth of axon bundles in peripheral nerve systems without deformation of the nerves.

Droplet Geometry

Our proposed DBE technique takes advantage of a wetting barrier phenomenon occurred at a four-phase interface. Generally, the shape of a liquid droplet on a homogenous solid substrate is primarily governed by the surface free energy of the substrate. However, for a four-phase interface such as a vapor-liquid-hydrophilic surface-hydrophobic surface interface, the spreading of the liquid is restricted by the wetting barrier formed at the boundary between the hydrophilic region and the hydrophobic region. Consequently, the contact angle of the droplet can vary within a certain range, with a maximum contact angle corresponding to the equilibrium contact angle of the hydrophobic surface.

Based on this principle, we designed an analytical model to determine the maximum volume of SU-8 sustained in a pre-defined pattern as well as to predict the length variation of waveguides. Our model assumed the droplet had a perfect spherical shape with a diameter of R. At equilibrium, the volume of the SU-8 solution can be calculated using the following Equation (1):

$$V = \tfrac{1}{3}\pi R^3 (2 - 3\cos\alpha + \cos^3\alpha), \tag{1}$$

where V is the actual volume of SU-8 in the droplet, R is the diameter of the droplet of SU-8, and α is the equilibrium contact angle of the SU-8 droplet after pre baking. The diameter of the interface between the droplet and the $O_2$ plasma-treated PDMS surface, d, is pre-defined. The relationship between R and d is given by the following Equation (2):

$$R = \frac{d}{2\sin\alpha} \tag{2}$$

By substituting R with d in Equation (1), the liquid volume V can be rewritten as a function of the pre-defined interfacial diameter d and the equilibrium contact angle of droplet α, as in Equation (3):

$$V = \frac{1}{24}\pi d^3 \frac{(2 + \cos\alpha)(1 - \cos\alpha)^2}{\sin^2\alpha} \quad (3)$$

Once a shape of the droplet is determined by SU-8 volume, three parameters can be controlled by the mask diameter and the distance from the center of the droplet of the mask aperture, including tip diameter, bottom diameter, and the length of the waveguide. The base diameter of the waveguide is associated with the diameter of the mask, and the tip size is closely linked with the tapered angle of the waveguide and the thickness of the SU-8 layer on top of the mask aperture. Since the tapered angle is controlled by the distance between the absorber on the photo mask and the top of the SU-8, the only controllable parameter is the thickness of the SU-8 layer. Because the thickness of the SU-8 varies in a predictable manner in the SU-8 droplet structure, the length and the tip diameter can be designed by tuning the distance between the mask opening and the center of the droplet.

The maximum height of the droplet, $h_{Max}$, can be estimated using a trigonometric relationship of Equation (4):

$$h_{Max} = R - \frac{d}{2\tan\alpha} \quad (4)$$

Once the value of $h_{Max}$ is estimated from the applied volume, a parameter h, which is a height at the distance b from the center of the droplet, can be calculated using Equation (5):

$$h = \frac{\sqrt{\left(\frac{d}{2}\right)^4 + h_{Max}^2\left(2\left(\frac{d}{2}\right)^2 - 4b^2 + 1\right)} - \left(\frac{d}{2}\right)^2 + h_{Max}^2}{2h_{Max}} \quad (5)$$

It has been found that the estimated height values predicted with Equation (5) typically agree with measured height values to within 5%.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A brain implantable neural prosthetic device, comprising:
   a two-dimensional array of light emitting diodes (LEDs) spaced apart in a plane, the array includes at least three LEDs with wavelengths in a visible spectrum per array side;
   a planar, transparent flexible substrate disposed parallel to the plane and facing the array of LEDs; and
   a plurality of transparent SU-8 needle-shaped waveguides in a one-to-one correspondence with the array of LEDs,
      each waveguide having a first end facing the flexible substrate and a second end facing away from the flexible substrate,
      each waveguide extending in a direction perpendicular to the plane of the LEDs, the waveguides and the LEDs being on opposite sides of the flexible substrate,
      each waveguide configured to receive light from a respective LED through its first end, transmit the light from its first end to its second end, and expel the light at its second end,
      the second ends of the waveguides configured to collectively define a sphere and lie on an interior concave surface portion of the sphere, in an unbent state of the flexible substrate,
      each waveguide defining a length from its first end to its second end;
      wherein at least two of the waveguides per array side have different lengths.

2. The device of claim 1, wherein:
   at least one waveguide is tapered to have a smaller cross-sectional area at its second end than at its first end; and
   the cross-sectional area of the first end of the waveguide is smaller than a cross-sectional area of a corresponding LED.

3. The device of claim 1, wherein the waveguides are configured to penetrate brain tissue without breaking.

4. The device of claim 1, wherein the flexible substrate is formed from a silicon-based organic polymer that is transparent over a range of emission wavelengths of the LEDs.

5. The device of claim 1, wherein:
   the LEDs are independently controllable; and
   the LEDs emit light at a first wavelength between 450 nm and 495 nm.

6. The device of claim 1, wherein:
   the LEDs and waveguides are positioned at a first end of a flexible circuit; and
   the LEDs are electrically connected to metal contacts at a second end of the flexible circuit opposite the first end.

7. The device of claim 1, further comprising a metallic layer disposed on the waveguides.

8. The device of claim 7, wherein the metallic layer extends from the first ends of the waveguides toward the second ends of the waveguides, but does not extend over the second ends of the waveguides.

9. The device of claim 8, further comprising:
   an oxide layer disposed directly on the waveguides and extending from the first ends to the second ends of the waveguides and over the second ends of the waveguides;
   a first polymer layer disposed directly on the oxide layer and extending from the first ends to the second ends over the second ends of the waveguides, the metallic layer being disposed directly on the first polymer layer; and
   a second polymer layer disposed directly on the metallic layer and extending from the first ends of the waveguides toward the second ends of the waveguides, but not extending over the second ends of the waveguides, and exposing a portion of the metallic layer.

10. A brain implantable neural prosthetic device, comprising:
- a two-dimensional array of light emitting diodes (LEDs) spaced apart in a plane, the array includes at least three LEDs per array side, the LEDs being independently controllable, the LEDs being configured to emit light at a first wavelength between 450 nm and 495 nm;
- a planar, transparent flexible substrate disposed parallel to the plane and facing the array of LEDs;
- a plurality of transparent SU-8 needle-shaped waveguides in a one-to-one correspondence with the array of LEDs,
  - each waveguide having a first end facing the flexible substrate and a second end facing away from the flexible substrate,
  - each waveguide extending in a direction perpendicular to the plane of the LEDs,
  - the waveguides and the LEDs being on opposite sides of the flexible substrate,
  - each waveguide configured to receive light from a respective LED through its first end, transmit the light from its first end to its second end, and expel the light at its second end,
- the second ends of the waveguides configured to collectively define a sphere and lie on an interior concave surface portion of the sphere, in an unbent state of the flexible substrate,
- each waveguide defining a length from its first end to its second end;
  - wherein at least two of the waveguides per array side have different lengths;
- an oxide layer disposed directly on the waveguides and extending from the first ends to the second ends of the waveguides and over the second ends of the waveguides;
- a first polymer layer disposed directly on the oxide layer and extending from the first ends to the second ends over the second ends of the waveguides;
- a metallic layer being disposed directly on the first polymer layer and extending from the first ends of the waveguides toward the second ends of the waveguides, but not extending over the second ends of the waveguides; and
- a second polymer layer disposed directly on the metallic layer and extending from the first ends of the waveguides toward the second ends of the waveguides, but not extending over the second ends of the waveguides, and exposing a portion of the metallic layer.

11. The neural prosthetic device of claim 10, wherein the flexible substrate is formed from polydimethylsiloxane (PDMS).

* * * * *